United States Patent
Gardeski et al.

(10) Patent No.: US 10,357,647 B2
(45) Date of Patent: Jul. 23, 2019

(54) TUNNELING TOOL

(71) Applicant: Medtronic, Inc., Minneapolis, MN (US)

(72) Inventors: Kenneth C. Gardeski, Plymouth, MN (US); James K. Carney, Roseville, MN (US); Melissa G. T. Christie, Andover, MN (US); Michael R. Leners, St. Francis, MN (US); Lonnie D. Ronning, Coon Rapids, MN (US); Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1009 days.

(21) Appl. No.: 14/293,382

(22) Filed: Jun. 2, 2014

(65) Prior Publication Data
US 2015/0343197 A1    Dec. 3, 2015

(51) Int. Cl.
*A61N 1/05*      (2006.01)
*A61B 17/34*     (2006.01)
(Continued)

(52) U.S. Cl.
CPC ............ *A61N 1/05* (2013.01); *A61B 17/3468* (2013.01); *A61B 18/1492* (2013.01); *A61M 25/0068* (2013.01); *A61N 1/0504* (2013.01); *A61B 2017/320056* (2013.01); *A61B 2017/3454* (2013.01); *A61B 2018/00333* (2013.01); *A61M 25/007* (2013.01); *A61M 25/0069* (2013.01); *A61M 2025/0092* (2013.01); *A61N 1/0563* (2013.01)

(58) Field of Classification Search
CPC .... A61B 17/3468; A61B 2017/320056; A61B 2017/3456; A61M 25/0068; A61M 25/09; A61M 2025/091
See application file for complete search history.

(56) References Cited

U.S. PATENT DOCUMENTS 3,496,932 A    2/1970    Prisk et al.
4,832,687 A    5/1989    Smith, III
(Continued)

FOREIGN PATENT DOCUMENTS

CN    101085388 A    12/2007
JP    2013116351 A    6/2013

OTHER PUBLICATIONS (PCT/US2015/033121) PCT Notification of Transmittal of the International Search Report and the Written Opinion of the International Searching Authority, dated Sep. 18, 2015, 9 pages.
(Continued)

*Primary Examiner* — Alexander J Orkin

(57) ABSTRACT

A method and device for implanting a medical lead. The device includes an elongate shaft defining a major longitudinal axis and including a proximal end and a distal end. A necked portion coupled to and extending from the distal end is included, the necked portion defines a first thickness and a substantially planar surface, the necked portion being at least resiliently movable in a direction normal to the major longitudinal axis. A tip disposed at the distal end of the necked portion is included, the tip defining a second thickness greater than the first thickness.

15 Claims, 7 Drawing Sheets

(51) Int. Cl.
*A61B 18/14* (2006.01)
*A61M 25/00* (2006.01)
A61B 17/32 (2006.01)
A61B 18/00 (2006.01)

(56) References Cited

U.S. PATENT DOCUMENTS

| | | | | |
|---|---|---|---|---|
| 5,487,757 | A * | 1/1996 | Truckai | A61B 18/1492 |
| | | | | 604/264 |
| 5,522,818 | A | 6/1996 | Keith et al. | |
| 5,571,093 | A * | 11/1996 | Cruz | A61M 25/0026 |
| | | | | 604/264 |
| 5,944,732 | A | 8/1999 | Raulerson et al. | |
| 6,405,733 | B1 * | 6/2002 | Fogarty | A61B 90/39 |
| | | | | 128/899 |
| 7,191,015 | B2 | 3/2007 | Lamson et al. | |
| 7,632,241 | B2 | 12/2009 | Raijman et al. | |
| 8,308,793 | B2 | 11/2012 | Meyer et al. | |
| 8,323,227 | B2 | 12/2012 | Hamatake et al. | |
| 8,374,680 | B2 | 2/2013 | Thompson | |
| 8,460,331 | B2 | 6/2013 | Chin | |
| 8,574,192 | B2 | 11/2013 | Haarala et al. | |
| 8,636,694 | B2 | 1/2014 | Neidert et al. | |
| 2005/0261663 | A1 * | 11/2005 | Patterson | A61M 25/008 |
| | | | | 604/508 |
| 2006/0122458 | A1 * | 6/2006 | Bleich | A61B 17/1671 |
| | | | | 600/101 |
| 2006/0259014 | A1 | 11/2006 | Yarger | |
| 2008/0275440 | A1 | 11/2008 | Kratoska et al. | |
| 2009/0030426 | A1 * | 1/2009 | Zinn | A61B 17/3415 |
| | | | | 606/108 |
| 2009/0276022 | A1 | 11/2009 | Burnes et al. | |
| 2010/0082033 | A1 * | 4/2010 | Germain | A61B 17/1642 |
| | | | | 606/79 |
| 2010/0113963 | A1 | 5/2010 | Smits et al. | |
| 2010/0125194 | A1 | 5/2010 | Bonner et al. | |
| 2012/0016377 | A1 | 1/2012 | Geroy | |
| 2014/0094645 | A1 | 4/2014 | LaFontaine et al. | |

OTHER PUBLICATIONS

Medtronic, 6996T Tunneling Tool, Technical Manual, UCX19842001 198462001, Sep. 2001.
E. Cigna, et al., A new technique for substernal colon transposition with a breast dissector: Report of 39 cases, Journal of Plastic, Reconstructive & Aesthetic Surgery (2006) 59, pp. 343-346.
Gardeski et al., "Tunneling Tool", Chinese Patent Application 201580026781.3, First Chinese Office Action Dispatched Aug. 2, 2018, 7 pages.

* cited by examiner

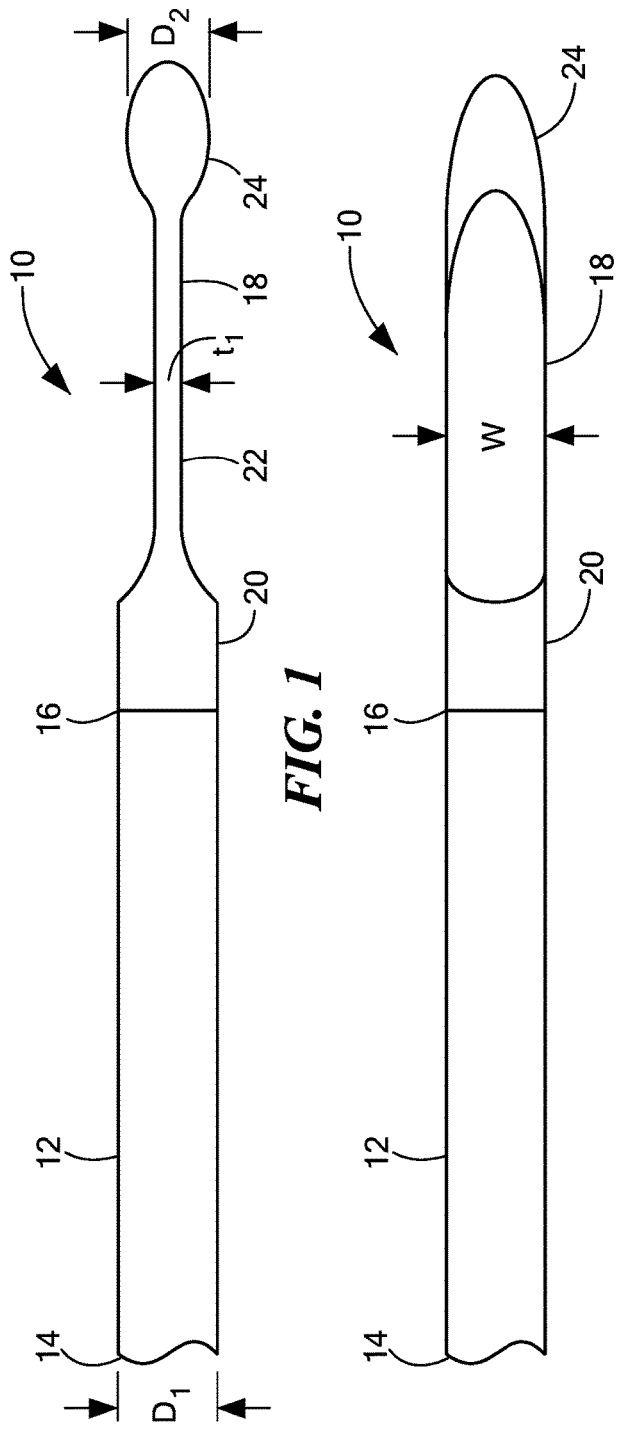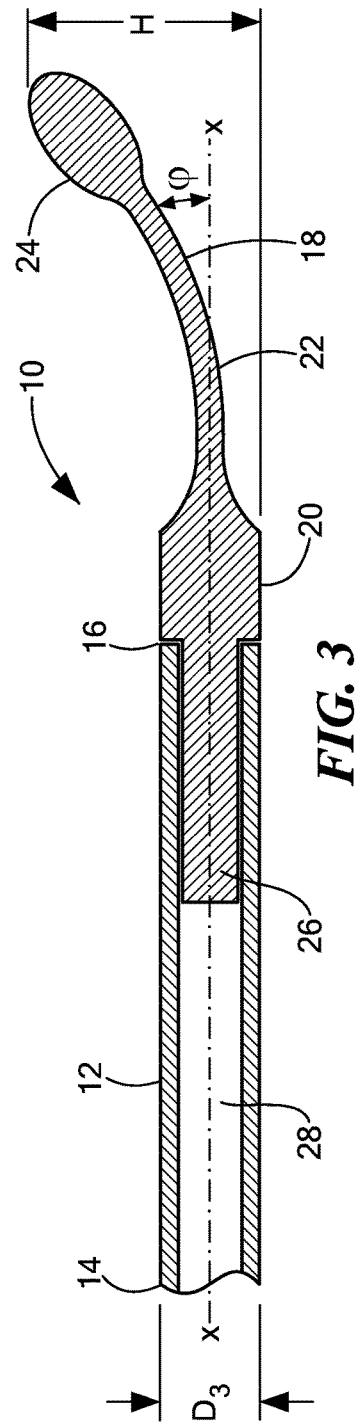

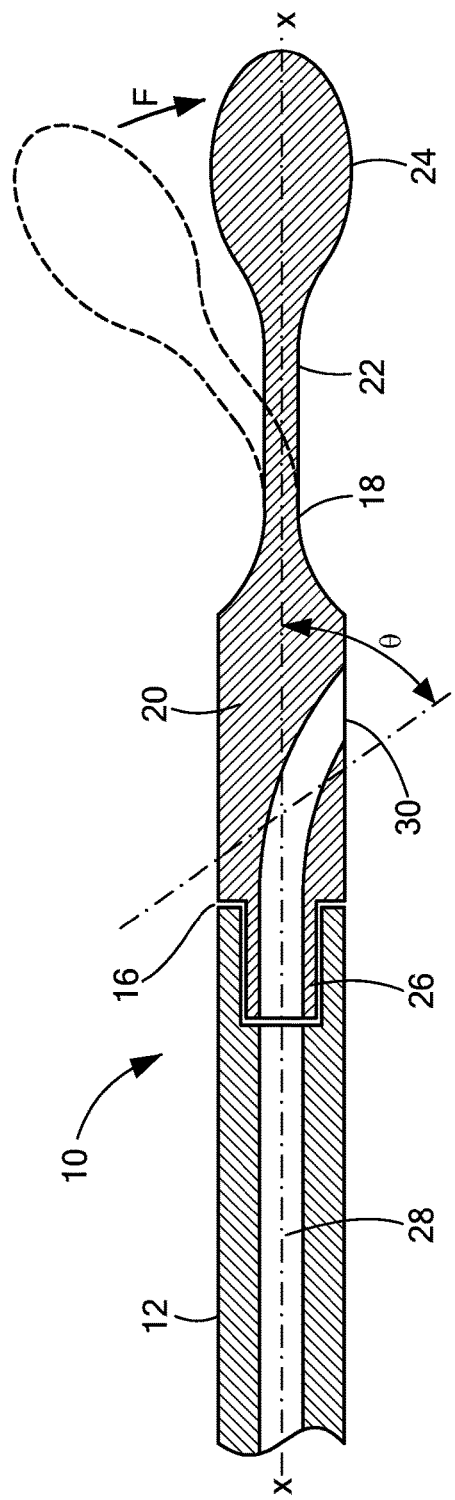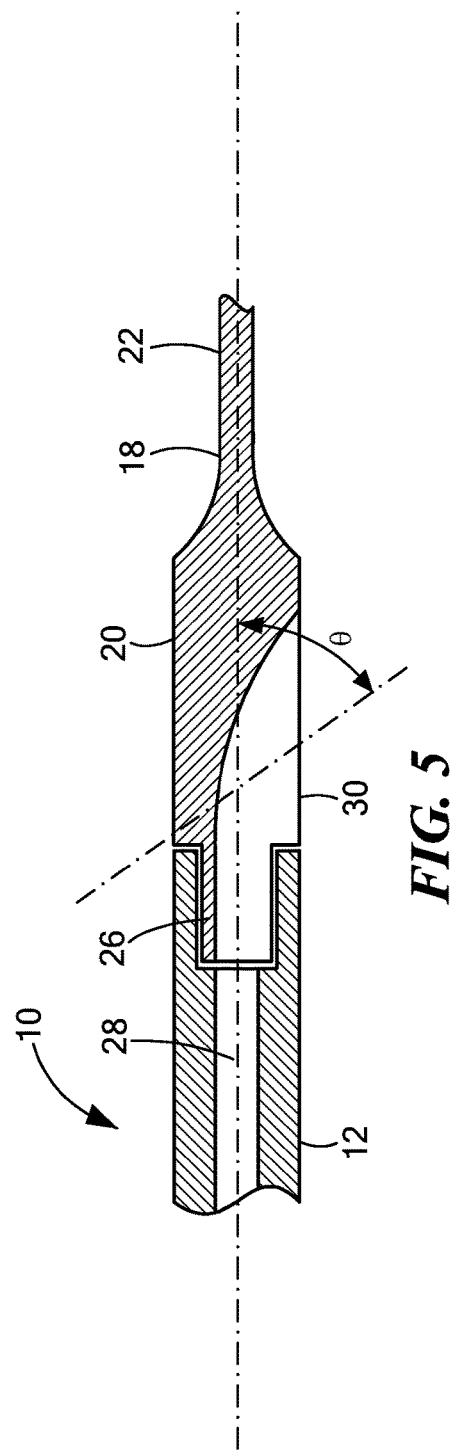

TUNNELING TOOL

CROSS-REFERENCE TO RELATED APPLICATION n/a

STATEMENT REGARDING FEDERALLY SPONSORED RESEARCH OR DEVELOPMENT n/a

FIELD OF THE INVENTION

The present application relates to a medical device and method for creating a pathway for insertion of medical leads within a patient.

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a small battery powered electrical shock device, may include an electrical housing, or can electrode, that is coupled to one or more electrical lead wires placed within the heart. If an arrhythmia is sensed, the ICD may send a pulse via the electrical lead wires to shock the heart and restore its normal rhythm.

Subcutaneous implantable cardioverter-defibrillator (SubQ ICD) systems have been devised to deliver electrical impulses to the heart by the use of a defibrillation lead placed subcutaneously on the torso. However, the SubQ ICD is large and requires an output of around 80J of energy to be effective. The large size of the SubQ ICD compromises patient comfort and has been known to erode through the skin after implantation. In addition, the SubQ ICD system is incapable of delivering anti-tachycardia pacing (ATP), which is a standard therapy in transvenous ICDs to painlessly terminate lethal tachyarrhythmias.

Owing to the large size and cost of the SubQ ICD device, and its inability to deliver painless therapy, it is desirable to provide method of implantation of a medical lead that is minimally traumatic, and also provides a pathway for a medical lead that does not require such a large output of energy for defibrillation. While tunneling tools have been devised to create a subcutaneous pathway for implantation of medical leads, current tunneling tools have fixed configurations and thus provide limited maneuverability through the tough tissues within the torso. Moreover, the pathway from the center of the chest to a position proximate the heart includes sensitive and easily punctured tissues, such as the heart and the lungs. Thus, it is desirable to provide a flexible tunneling tool that facilitates the creation of a pathway for insertion of medical lead without damaging sensitive tissue.

SUMMARY OF THE INVENTION

The present application advantageously provides a method and medical device for implanting a medical lead. The device includes an elongate shaft defining a major longitudinal axis and including a proximal end and a distal end. A necked portion coupled to and extending from the distal end is included, the necked portion defines a first thickness and a substantially planar surface, the necked portion being at least resiliently movable in a direction normal to the major longitudinal axis. A tip disposed at the distal end of the necked portion is included, the tip defining a second thickness greater than the first thickness.

In another embodiment, the method includes substernally advancing a medical device from a first position proximate the xiphoid process to a second position proximate the cranial end of the sternum. The medical device includes an elongate shaft having a proximal end and a distal end, the elongate malleable shaft defining a major longitudinal axis. A necked portion coupled to and extending from the distal end is included, the necked portion defines a first thickness and a substantially planar surface, the necked portion being flexible in a direction normal to the major longitudinal axis. A tip coupled to the distal end of the necked portion is included, the tip defining a second thickness greater than the first thickness.

In another embodiment, the method includes advancing a medical device from a first position proximate the xiphoid process to a second position proximate the pericardium. The medical device includes an elongate malleable shaft having a proximal end and a distal end, the elongate malleable shaft defining a major longitudinal axis. A necked portion coupled to and extending from the distal end is included, the necked portion defines a first thickness and a substantially planar surface, the necked portion being flexible in a direction normal to the major longitudinal axis. A lumen extending from the proximal end to the distal end is included. A port in fluid communication with the lumen is included. A tip coupled to the distal end of the necked portion is included, the tip defining a second thickness greater than the first thickness.

BRIEF DESCRIPTION OF THE DRAWINGS

A more complete understanding of the present application, and the attendant advantages and features thereof, will be more readily understood by reference to the following detailed description when considered in conjunction with the accompanying drawings wherein:

FIG. 1 is a side view of a medical device constructed in accordance with the principles of the present application;

FIG. 2 is a top view of the medical device shown in FIG. 1;

FIG. 3 is a side cross-sectional view of the medical device shown in FIG. 1 with the necked portion biased in an arcuate configuration;

FIG. 4 is a side cross-sectional view of another medical device constructed in accordance with the principles of the present application;

FIG. 5 is a side cross-sectional view of another medical device constructed in accordance with the principles of the present application;

DETAILED DESCRIPTION OF THE INVENTION

Figure 6:
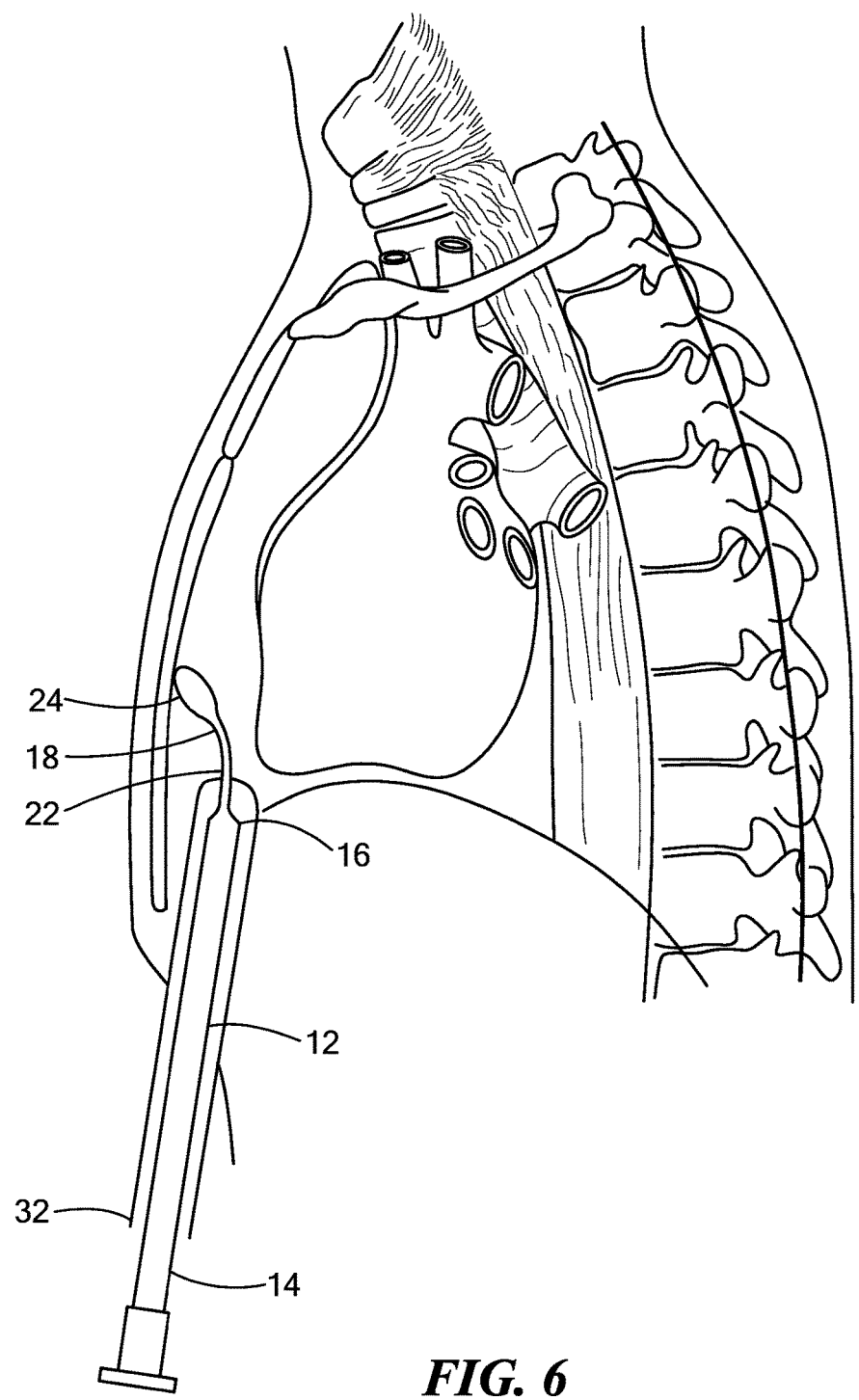
FIG. 6 is a side cross-sectional view of a patient's torso with the medical device of either FIGS. 1-5 advanced underneath the sternum.

Referring now to the drawings in which like reference designators refer to like elements, there is shown in FIGS. 1-2 an exemplary medical device constructed in accordance with the principles of the present application and designated generally as "10." The medical device 10 may be sized to be received within a human or animal patient, and in particular, the torso of a human. The medical device 10 may include an elongate solid or hollow shaft 12, sized and configured to penetrate the fascia and the anterior mediastinum proximate the xiphoid process. In other configurations, the elongate shaft 12 may be a flexible catheter sized to be received and advanced within the vasculature. The elongate shaft 12 may be composed malleable materials, for example, grade 316L stainless steel, or other alloys that facilitate the elongate shaft 12 retaining its configuration when manipulated from a first configuration, for example a linear configuration, to a second configuration, for example, a curvilinear configuration. Alternatively, the elongate shaft 12 may be composed of flexible and/or superelastic materials such as in the case in which the elongate shaft 12 is an endovascular catheter. In other configurations, the elongate shaft 12 may be composed of rigid materials such as stainless steel, such that the shaft is inflexible. The elongate shaft 12 may include a proximal end 14 and a distal end 16. The proximal end 14 may be coupled to a handle (not shown) and may optionally be in fluid communication with a fluid source via one or more umbilicals, and/or mechanically coupled to other treatment delivery modalities such as a syringe or needle advancement device.

Coupled to the distal end 16 of the elongate shaft 12 may be a necked portion 18. The necked portion 18 may be mechanically coupled, molded, permanently affixed, or removeably engageable with the distal end 16 of the elongate shaft 12 such that the necked portion 18 extends a longitudinal distance away from the distal end 16. In an exemplary embodiment, the length of the necked portion 18 may be less than the length of the elongate shaft 12. The necked portion 18 may include a proximal portion 20, which abuts the distal end 16 and may define the same thickness and/or diameter ($D_1$) as the outer diameter of elongate shaft 12. The proximal portion 20 may be substantially rigid and immovable with respect to the elongate shaft 12 when the proximal portion 20 is engaged to the distal end 16 of the elongate shaft 12. Longitudinally extending from the proximal portion 20 is stem 22. The stem 22 may define a thickness ($t_1$) that is less than the thickness and/or diameter ($D_1$) of the elongate shaft 12. An exemplary thickness ($t_1$) may be 0.024 inches and may range from 0.005 inches to 0.05 inches depending on the application. In an exemplary configuration, the proximal portion 20 tapers in thickness as it extends into the stem 22. The stem 22 may define a substantially planar surface along substantially its entire length and width (W) (best seen in FIG. 2) larger than its thickness ($t_1$). The stem 22 may be composed of spring tempered stainless steel, or any resiliently movable material, such that the stem 22 is resiliently movable in the direction normal to the major longitudinal axis, which is illustrated by the arrow in FIG. 4 next to the force "F", and is substantially or completely immovable in the direction binormal to the major longitudinal axis, which in the drawing shown in FIG. 4 would represent the stem 22 being immovable in the direction moving into the page and out of the page, as discussed in more detail below.

Continuing to refer to FIGS. 1 and 2, extending longitudinally from the stem 22 is the tip 24. The tip 24 may be composed of, for example, stainless steel, or softer materials depending on the particular application. In an exemplary configuration, the tip 24 defines a blunted atraumatic surface such that when the tip 24 is traversing the anatomy or vasculature of a patient, damage to the surrounding tissue is minimized. For example, the tip 24 may define a substantially ovoid, spherical, or hemispherical tip such that it may slide along the surface of the internal anatomy of a patient, and in a particular application, the posterior surface of the sternum. The tip 24 may define a thickness and/or diameter ($D_2$) that is greater than the thickness ($t_1$) of the stem and greater than, less than, or equal to the diameter ($D_1$) of the elongate shaft 12 depending on the particular application.

Referring now to FIG. 3, the proximal portion 20 of the necked portion 18 may define a proximal engagement 26 extending a distance into the distal end 16 of the elongate shaft 12. In particular, the elongate shaft 12 may define a lumen 28 extending from the proximal end 14 out through the distal end 16. In the configuration shown in FIG. 3, the proximal engagement 28 extends a distance into the lumen 28 to plug the lumen 28, and to attach the necked portion 18 to the elongate shaft 12. In particular, the lumen 28 may define a diameter ($D_3$) less than diameter ($D_1$) and sized to receive the proximal engagement 26. The proximal engagement 26 may be friction fit within the lumen or affixed by an adhesive such that it is not removeable from the lumen 28. Alternatively, the proximal engagement 26 may be matable and detachable to the tunneling tool 12, such that the necked portion 18 may be a modular component. In particular, the proximal engagement 26 may include a mating element (not shown) engageable with a portion of the elongate shaft 12, for example a recess (not shown). For example, the proximal engagement 26 may include a bayonet type connection with the elongate shaft 12 such that it can be readily attached and removed. As another example, the proximal engagement 26 and distal portion of the lumen 28 may be threaded such that the proximal engagement is screwed into the elongate shaft 12. In such configurations, various necked portions 18 may be interchangeable within the lumen 28 depending on the desired use of the elongate shaft 12. The proximal engagement 26 may further define a fluid-tight seal within the lumen 28, such that as the elongate shaft 12 is advanced within the patient, air and fluids are prevented from entering the patient, for example, the heart, from outside the body.

Continuing to refer to FIG. 3, the stem 22 may be biased in an arcuate or otherwise curved configuration with respect to the major longitudinal axis "x" defined by the elongate shaft 12. In particular, the stem 22 may be biased at an angle "φ," which may be, for example, approximately 30 degrees, but may be any angle, for example, between 0 and 90 degrees. The bias of the stem 22 may be caused by, for example, the stem 22 being composed of a spring tempered steel, which imparts a curve on the stem 22 in the direction normal to the major longitudinal axis "x." In an exemplary configuration the necked portion 18 may define a height "H," defined as the distance between the bottom of the elongate shaft 12 and the top of the tip 24 when the elongate shaft is positioned as shown in FIG. 3. The height "H" may vary depending on the degree of bias imparted by the stem 22 on the necked portion 18. The necked portion 18, and in particular the stem 22, may be resiliently movable in response to a force applied to the tip 24. In particular, a force applied to the tip 24 in direction "F" (as shown in FIG. 4, for example) may cause the tip 24 and the stem 22 to pivot or otherwise move in a direction normal to and toward the major longitudinal axis "x," while being substantially immovable in the direction binomial to the major longitudinal axis "x." That is, the stem 22 is movable in a single arc with respect to the major longitudinal axis "x." Because the stem 22 is biased in an arcuate configuration, the tip 24 resists the force "F," such that when the force "F" is removed, the tip 24 and the stem 22 spring back to its biased arcuate configuration as shown in FIG. 3.

Referring now to FIG. 4, in another configuration, the lumen 28 may extend out through the distal end 16 and into the proximal extension 26, such that the proximal portion 20 and the elongate shaft 12 are in fluid communication. In the exemplary embodiment shown in FIG. 4, the lumen 28 is curved in at least part of the proximal portion 20 such that it defines a port 30 proximal to the stem 22. In another exemplary embodiment, the lumen 28 may extend co-axially into the proximal portion 20 and extend out through the tip 24. In the configuration shown in FIG. 4, the port 30 is substantially the same diameter as the diameter of the lumen 28 such that a guidewire (not shown) may be removeably inserted within the lumen 28 and exit out the port 30. Alternatively, as shown in FIG. 5, the port 30 may be define a larger space or diameter to that of the lumen 30 to accommodate an instrument larger than a guidewire. For example, a needle (not shown) or another medical device with a larger diameter distal end compared to the diameter of a guidewire may be slid through the lumen 28 and the distal end of the needle may be slid out through the port 30. In both the embodiments shown in FIG. 4 and FIG. 5, the port 30 is defined at an angle "A" with respect to the major longitudinal axis "x." For example, as shown in FIGS. 4 and 5, the port 30 is disposed at an angle "θ" of approximately 30 degrees with respect to the major longitudinal axis "x," and in other embodiments, the port 30 may be disposed at angle "θ," for example, approximately 5 to 90 degrees depending on the particular use of the device 10. The port 30 may be located on the side opposite the curved segment of necked portion 18. The port 30 may alternatively be positioned on the side of the proximal portion 20 with the curved segment of necked portion 18 or along any portion of the elongate shaft 12 or the necked potion 18. In an exemplary configuration, the port 30 is positioned on the side of the necked portion 18 opposite the curved segment of the necked portion, to prevent tissue from being lodged within the port 30 as the elongate shaft 12 is advanced cranially.

Referring now to FIGS. 6-10, in an exemplary use of the device 10, the device 10 may be slid through a previously placed introducer device 32, which may include, for example, a sterile sheath with a dilator and guidewire and/or a catheter 34 with an internal lumen sized to receive the elongate shaft 12. In particular, the surgeon may create an incision proximate the xiphoid process, insert the introducer device 32 and advance the device 10 underneath the sternum either through the introducer device 32 or through the lumen of the catheter 34, which may be first slid through the introducer device (Step S100). The elongate shaft 12 may be oriented such that as the tip 24 exits the introducer device 32, the necked portion 18 is biased in its arcuate configuration to position the tip 24 to be in contact with the posterior surface of the sternum. Owing to the atraumatic shape of the tip 24, as the elongate shaft 12 is advanced superiorly within the torso, the tip 22 may glide along the sternum and is angled away from the lungs and the heart as to avoid inadvertent puncturing of those organs. Additionally, because the stem 22 is substantially planar, thin, and immovable in the direction binomial to the major longitudinal axis "x," the necked portion 18 may be advanced smoothly as the elongate shaft 12 is advanced posteriorly, with limited interference form the surrounding tissue, allowing the surgeon to readily advance the device 10 to a desired tissue region with the body.

The elongate shaft 12 and the necked portion 18 may be advanced cranially from a position proximate the caudal end of the sternum, for example, the xiphoid process (shown in FIG. 6) to a position proximate the cranial end of the sternum (Step S102). Owing to the force applied by the posterior surface of the sternum on the tip 24, as the necked portion 18 is advanced cranially and the sternum curves backward, the stem 22 may be flexed in the direction "F" (as shown in FIG. 4), such that the necked portion 18 is substantially parallel with the major axis "x" of the elongate shaft. If the elongate shaft 12 is advanced farther cranial toward the manubrium, the tip 24 may bend toward the heart as it contacts the manubrium such that the opening 30 is angled toward the pericardium. The position of the tip 24 is identified in FIG. 7 as 24' when it is positioned for substernal implantation of a medical lead, for example, a defibrillation or pacing lead electrically coupled to a can electrode (not shown) configured to transmit defibrillation and/or pacing electrical impulses to the heart.

When the tip 24' is positioned proximate the pulmonary trunk or substantially axially positioned along the plane of the T4 vertebra, a guidewire (not shown) may be advanced through the lumen 28 and out through the port 30 of the configuration shown in FIG. 4 (Step S104). The elongate shaft 12 may then be withdrawn from the torso of the patient and a medical lead (not shown) may be advanced over the guidewire through the introducer device 32 and/or lumen of the catheter 34 and implanted underneath the sternum (Step S106). Alternatively, the elongate shaft 12 may be withdrawn from the introducer device 32 and/or catheter 34, and the guidewire may be fed through the lumen of the catheter 34. The catheter 34 may remain in place and the medical lead may be slid through the lumen of the catheter 34 over the guidewire.

Figure 7:
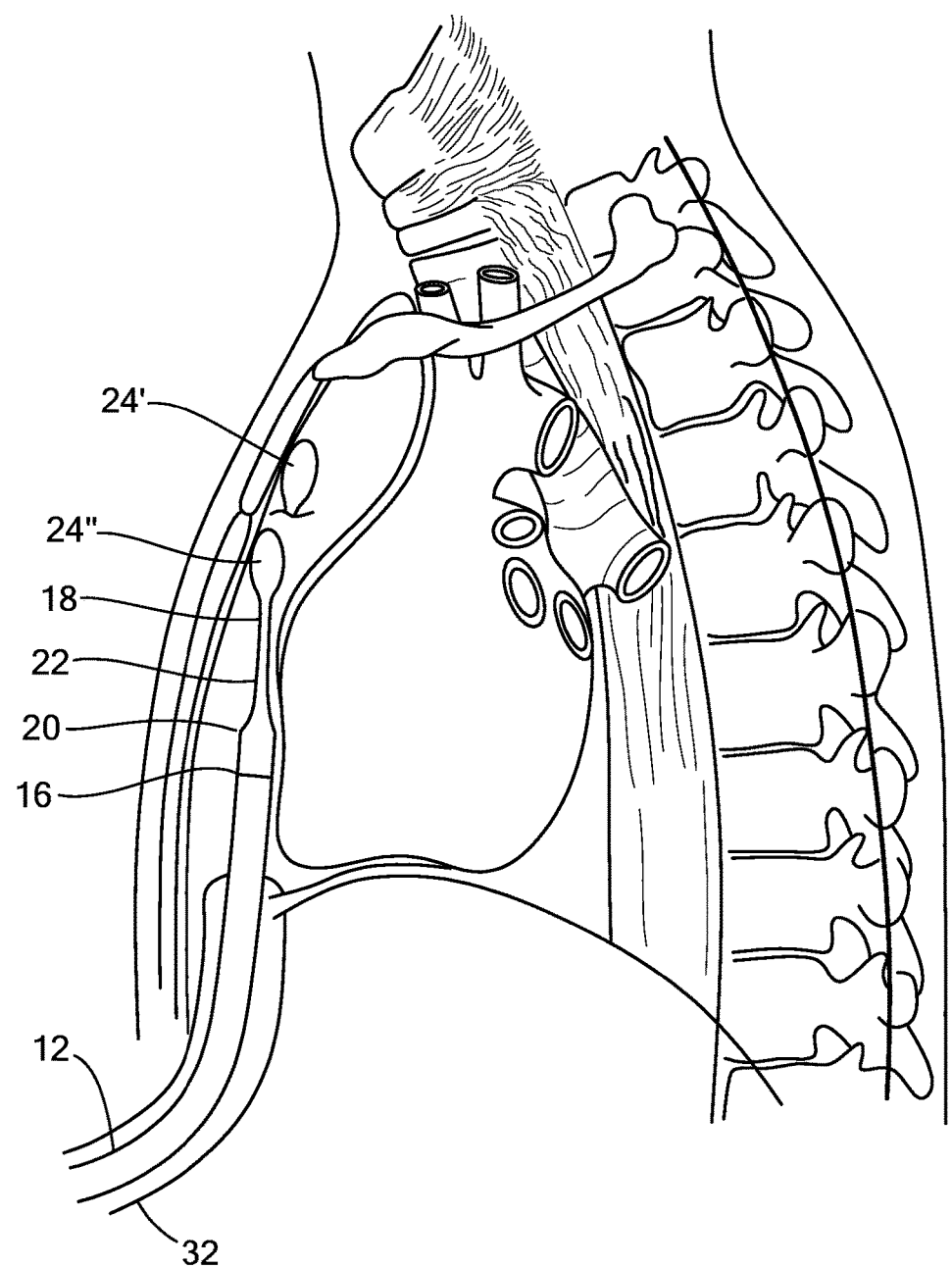
FIG. 7 is a side cross-sectional view of the medical device shown in FIG. 6 showing the medical device of either FIGS. 1-5 advanced to different locations underneath the sternum.
Figure 8:
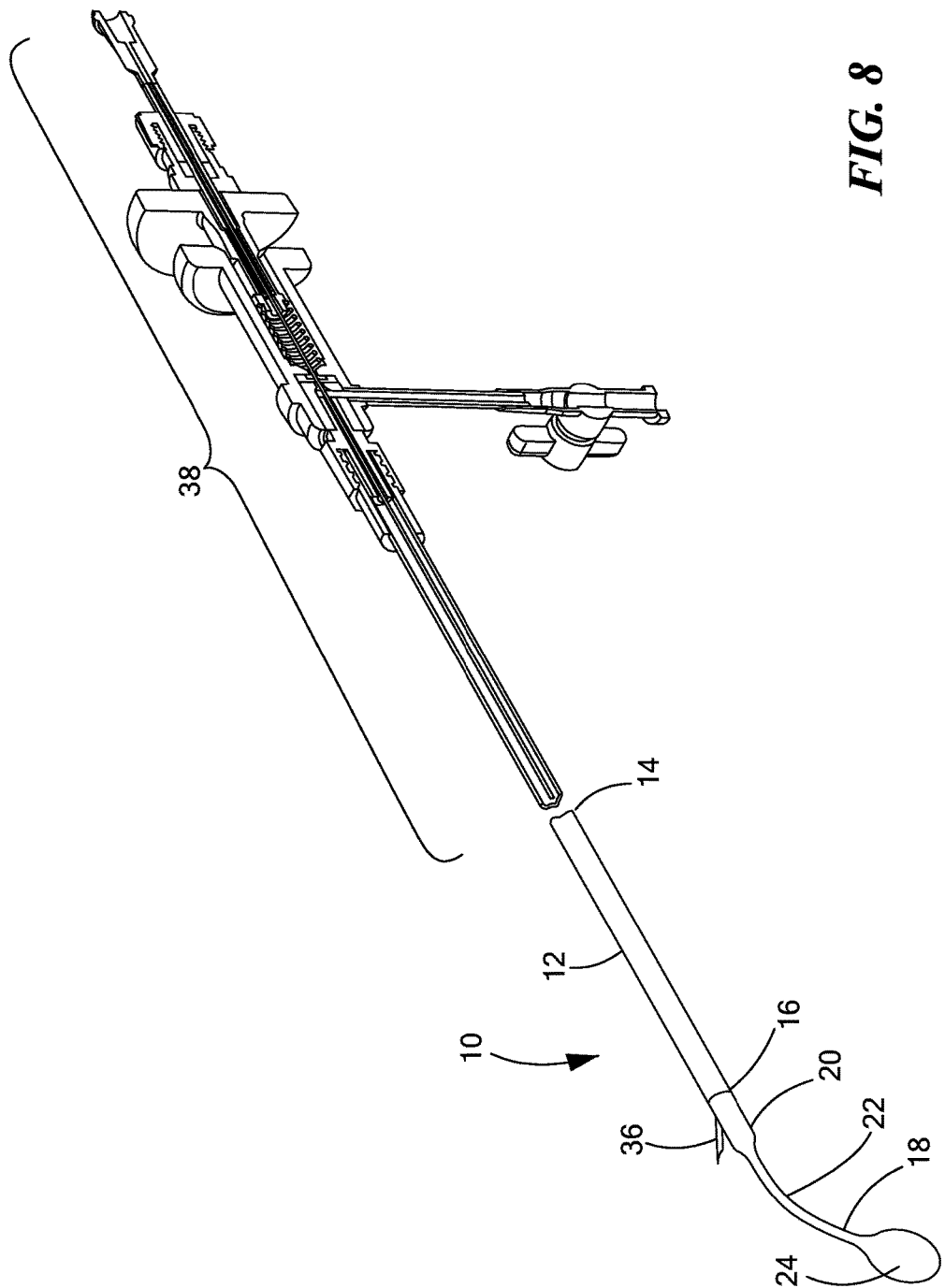
FIG. 8 is a side cross-sectional view of a needle injector coupled to the medical device shown in FIG. 5.

In another use of the device 10, the elongate shaft 12 may be advanced to a substernal position such that the necked portion 18, and in particular, the port 30 is positioned adjacent the pericardium. The position of the tip 24 is identified as tip 24" when it is positioned for insertion of a pericardial medical lead. As shown in FIG. 7, the elongate shaft 12 may be advanced to a position such that the tip 24 is positioned to be substantially parallel to the major longitudinal axis "x." To facilitate the surgeon in locating the proper position of the necked portion 18, the necked portion 18 may include radiopaque markers (not shown) or other markers visible under fluoroscopy. Alternatively, a handle (not shown) connected to the proximal end 14, may include a position sensor or other indicator, that displays the angle defined by the necked portion 18 with respect to the major longitudinal axis "x." For example, the position sensor may indicate when the angle "θ" is 0 degrees to indicate when the stem 22 is straight, which may indicate the position of the tip 24. When surgeon determines the desired positioning of the necked portion 18 with respect to the pericardium, a needle 36 (seen in FIG. 8) may be advanced through the lumen 28 and out through the port 30, which may be sized in accordance with the embodiment of the device 10 shown in FIG.

5. The needle 36 may then pierce the pericardium providing a pathway for insertion of a guidewire over which a medical lead may be inserted. In an exemplary configuration the needle 36 may be incorporated as part of an injection device 38 configured to precisely pierce the pericardium without penetrating the heart too deeply. An exemplary injection device 38 that may be configured to be coupled or otherwise incorporated with the elongate shaft 12 is disclosed is U.S. Pat. No. 8,636,694, the entirety of which is expressly incorporated herein by reference.

Figure 9:
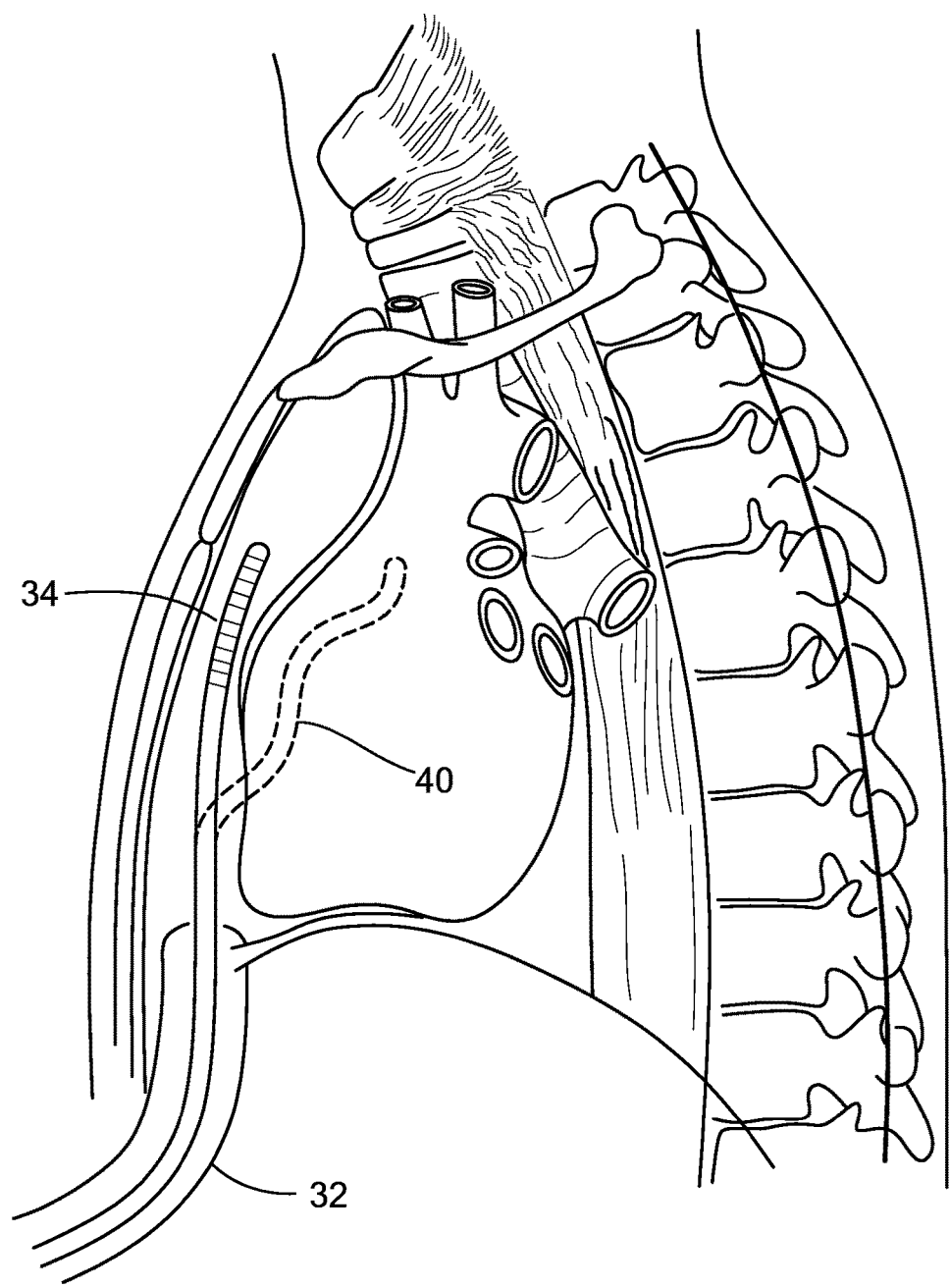
FIG. 9 is a side cross-sectional view of a patient's torso with guidewires positioned for advancement of a medical lead into the substernal space and the pericardium.
Figure 10:
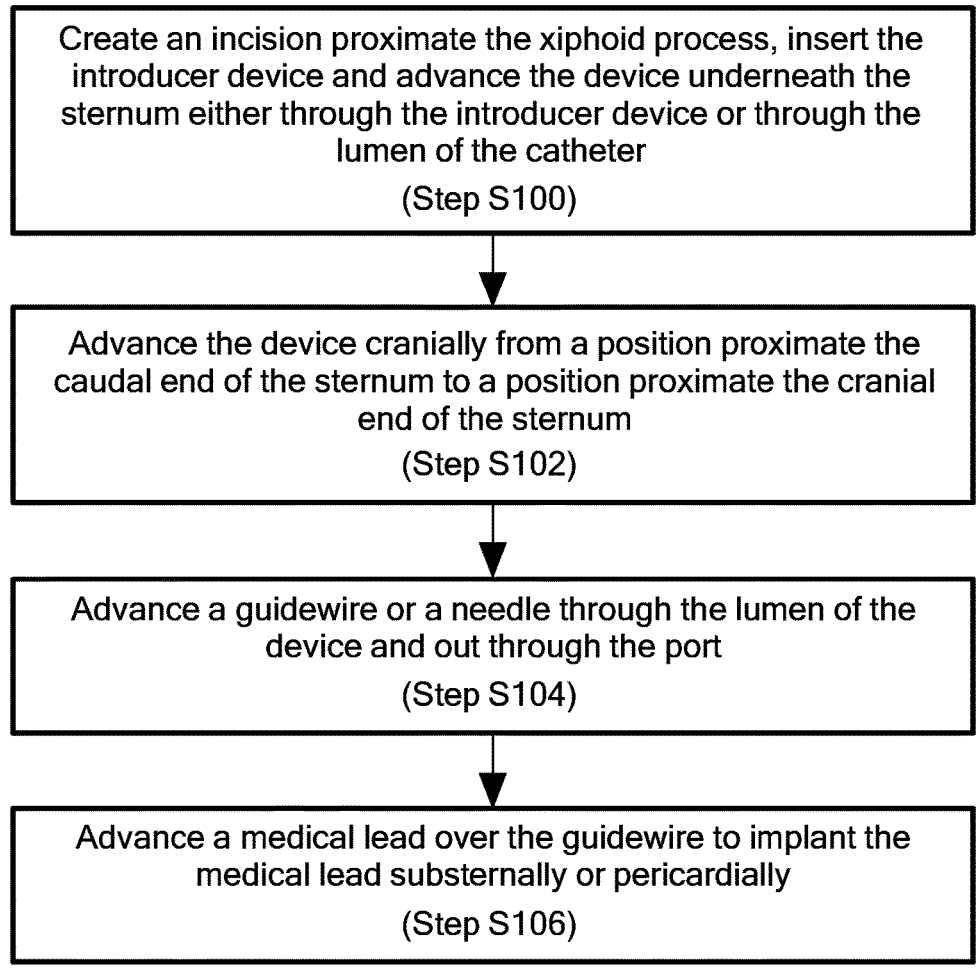
FIG. 10 is a flow chart of an exemplary method of creating a pathway for implantation of a medical lead constructed in accordance with the principles of the present application.

Referring now to FIG. 9, any size tip 24 may be used to tunnel through the mediastinum in accordance with the principles of the present application. For example, as discussed above, the necked portion 18 may be removeably affixed to the elongate shaft 12 such that necked portions 18 with varying sized tips 24 may be used. In a configuration in which a large tip 24 is used, the elongate shaft 12 may be advanced as described with respect to delivery of a substernal lead as discussed above, however, after the needle 36 is withdrawn from the lumen 28, the catheter 34 may be advanced through the sheath 32 to provide support for placement of the guidewire. In particular, the catheter 34, as shown in FIG. 9, may define a side port (not shown) similar the port 30, such that a guidewire 40 (shown in dashed lines to indicate its final position) may be advanced out through the lumen of the catheter 34 at angle for placement of a medical lead.

It is further contemplated that the device 10 may be used to place medical leads in any portion of the body of a human or animal patient. For example, the device 10 may be used to place stimulation leads around the vagal nerves by creating a pathway with the elongate shaft 12, which may be a flexible catheter composed of a superelastic material, from the carotid sheath to the vagal nerves. It is further contemplated that the device 10 may be used to place subcutaneous ICD's or other medical devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an elongate shaft defining a major longitudinal axis and including a proximal end and a distal end;
   a necked portion coupled to and extending from the distal end, the necked portion defining a first thickness and a substantially planar surface, the necked portion being at least resiliently movable in a direction normal to the major longitudinal axis; and
   a tip disposed at a distal end of the necked portion, the tip defining a second thickness greater than the first thickness, the tip is not movable in a direction binormal to the major longitudinal axis.

2. The medical device of claim 1, wherein the tip is substantially ovoid in shape.

3. The medical device of claim 1, wherein the tip is biased in an arcuate configuration.

4. The medical device of claim 1, wherein the elongate shaft is malleable, and defines a lumen extending from the proximal end to the distal end.

5. The medical device of claim 4, wherein the necked portion defines a port in fluid communication with the lumen.

6. The medical device of claim 5, wherein the port is disposed at an angle relative to the major longitudinal axis.

7. The medical device of claim 4, wherein the lumen is sized to receive at least one of a needle and a guidewire.

8. The medical device of claim 4, wherein the necked portion is removeably engageable to the distal end of the elongate shaft, and wherein the necked portion defines a lumen at least partially there through, and wherein when the necked portion is engaged to the distal end of the elongate shaft, the lumen of the elongate shaft is aligned with the lumen of the necked portion.

9. The medical device of claim 1, wherein the elongate shaft is a catheter sized to be inserted within the vasculature of a human patient.

10. The medical device of claim 1, wherein the necked portion extends a distance into a portion of the elongate shaft.

11. The medical device of claim 1, wherein the tip is composed of stainless steel.

12. The medical device of claim 1, wherein the necked portion is at least partially composed of spring tempered steel.

13. The medical device of claim 1, wherein the necked portion is removeably engageable to the distal end of the elongate shaft.

14. The medical device of claim 1, wherein the distal end of the elongate shaft defines an opening, and wherein at least a portion of the necked portion extends proximally into the opening.

15. A medical device, comprising:
   an elongate shaft defining a major longitudinal axis and including a proximal end and a distal end and defining a first diameter;
   a necked portion coupled to and extending from the distal end, the necked portion including:
      a proximal portion defining a second diameter substantially the same as the first diameter and defining a first thickness;
      a stem defining a second thickness less than the first thickness and a substantially planar surface, the stem being at least resiliently movable in a direction normal to the major longitudinal axis; and
      a tip disposed at a distal end of the stem, the tip defining a third thickness greater than the second thickness, the tip is not movable in a direction binormal to the major longitudinal axis.

* * * * *